United States Patent [19]

Vogel et al.

[11] Patent Number: 5,152,991
[45] Date of Patent: Oct. 6, 1992

[54] USE OF SELECTIVELY HYDROGENATED STYRENE/BUTADIENE COPOLYMERS IN COSMETIC AND PHARMACEUTICAL COMPOSITIONS

[75] Inventors: Friedrich Vogel, Wachenheim; Franz Frosch, Bad Durkheim; Horst Westenfelder, Durmersheim, all of Fed. Rep. of Germany

[73] Assignee: BASF Aktiengesellschaft, Ludwigshafen, Fed. Rep. of Germany

[21] Appl. No.: 714,702

[22] Filed: Jun. 13, 1991

[30] Foreign Application Priority Data

Jun. 13, 1990 [DE] Fed. Rep. of Germany ....... 4018875

[51] Int. Cl.$^5$ .................................................. A61K 7/00
[52] U.S. Cl. .................................. 424/401; 424/78.03; 514/844
[58] Field of Search ........................... 424/401, 63, 78; 514/844, 845, 846

[56] References Cited

U.S. PATENT DOCUMENTS 4,976,961 12/1990 Norbury et al. ..................... 424/401

FOREIGN PATENT DOCUMENTS 2423849 12/1974 Fed. Rep. of Germany .

Primary Examiner—Thurman K. Page
Assistant Examiner—Amy Hulina
Attorney, Agent, or Firm—Oblon, Spivak, McClelland, Maier & Neustadt

[57] ABSTRACT

Copolymers selectively hydrogenated on the olefinic double bond and composed of
A) 50 to 65% by weight styrene,
B) 35 to 50% by weight butadiene and
C) 0 to 5% by weight other copolymerizable monomers are used in cosmetic and pharmaceutical compositions.

5 Claims, No Drawings

USE OF SELECTIVELY HYDROGENATED STYRENE/BUTADIENE COPOLYMERS IN COSMETIC AND PHARMACEUTICAL COMPOSITIONS

The present invention relates to the use of copolymers which are selectively hydrogenated on the olefinic double bond and are composed of (A) 50 to 65% by weight styrene,
(B) 35 to 50% by weight butadiene and
(C) 0 to 5% by weight other copolymerizable monomers in cosmetic and pharmaceutical compositions.

The present invention also relates to cosmetic and pharmaceutical compositions which contain these copolymers.

The present invention also relates to cosmetic and pharmaceutical compositions which contain these copolymers.

Cosmetic and pharmaceutical compositions such as creams or oils for the skin very often have the disadvantage that they are too easily washed off. This is particularly unwanted in the case of sunscreen, baby and bath products. The optimal caring, healing or protective effect on the skin is not fully achieved and too much of these agents is used because they must be repeatedly reapplied.

DE-C 31 06 959 (1) relates to a process for preparing copolymers composed of 52 to 54 % by weight styrene and 46 to 48 % by weight butadiene by copolymerization of the monomers in aliphatic, cycloaliphatic or aromatic hydrocarbons with alkyllithium initiators in the presence of tetrahydrofuran, the polymerization being followed by selective hydrogenation of the double bond which derives from the butadiene in the copolymer by known processes, for example in the presence of transition metal catalysts such as nickel/ aluminum catalysts. These copolymers are used to improve the viscosity index of lubricant oils.

DE-A 24 23 849 (2) relates to a film-forming composition for local use on the skin in the form of an emulsion of a water-insoluble and of a water-soluble film-forming polymer. Among the water-insoluble polymers mentioned is a styrene/butadiene polymer with the monomers in the ratio 67:33 by weight. However, this film when applied to the skin can be washed off too easily with water.

It is an object of the present invention to provide cosmetic and pharmaceutical compositions which can be washed off the skin only with difficulty.

We have found that this object is achieved by using the copolymers defined in the first paragraph in cosmetic and pharmaceutical compositions.

The copolymers are composed of (A) 50 to 65% by weight, preferably 52 to 57% by weight, styrene
(B) 35 to 50% by weight, preferably 43 to 48% by weight, butadiene and
(C) 0 to 5% by weight other copolymerizable monomers.

They are prepared by polymerization of components A to C and subsequent selective hydrogenation on the olefinic double bond. The use of copolymers composed only of components A and B is preferred.

The polymerization and the hydrogenation are expediently carried out by the process described in (1). After the hydrogenation, not less than 95%, preferably not less than 97%, of the olefinic double bonds and not more than 5%, preferably not more than 3%, of the aromatic unsaturations ought to be hydrogenated.

The resulting copolymers are random polymers usually having a molecular weight in the range from 75,000 to 130,000.

Examples of other copolymerizable monomers C, which can be used to modify the properties of the copolymers, are methylstyrene, isoprene, chloroprene, isobutylene, ethylene, acrylonitrile, alkyl acrylates and methacrylates, vinyl acetate, vinyl chloride, vinylidene chloride and vinyl alkyl ethers.

Relevant cosmetic compositions are, in particular, skin creams such as skin-care creams, baby creams, barrier creams or sunscreen creams, oils such as bath oils, baby oils or sunscreen oils, ointments, lotions or cosmetics. Pharmaceutical compositions such as ointments or creams are used for administering active substances. The said cosmetic and pharmaceutical compositions can be either water-in-oil or oil-in-water emulsions or a combination of the two types.

The present invention also relates to cosmetic and pharmaceutical compositions which contain the said copolymers in an amount of from 1 to 20%, preferably 2 to 10%, of the total weight of the composition.

The conventional compositions and ingredients, and conventional emulsifiers, auxiliaries and additives such as stabilizers or preservatives for cosmetic and pharmaceutical compositions of these types are known to the person skilled in the art and thus need not be detailed here.

The cosmetic and pharmaceutical compositions containing the copolymers used according to the invention are distinguished by being difficult to wash off again with either pure or surfactant-containing water and are thus able to display fully their caring, healing or protective action on the skin. In addition, the copolymers used according to the invention have a distinct protective action on the skin because they impede the penetration of injurious substances.

Furthermore, the copolymers used according to the invention thicken the compositions containing them, which is evident from the higher viscosity and may simplify processing, storage and application of the compositions because it is easier to adjust the viscosity to the required range using the copolymers.

EXAMPLE 1

SUSCEPTIBILITY OF COSMETIC CREAM COMPOSITIONS TO WASHING OFF THE SKIN

A copolymer which had been prepared as described in (1) by polymerization of 53% by weight styrene with 47% by weight butadiene with sec-butyllithium as catalyst in a cyclohexane/tetrahydrofuran mixture and subsequent selective hydrogenation with hydrogen in the presence of nickel(II) acetylacetonate/triisobutylaluminum as catalyst was incorporated in cosmetic compositions. A dye (methylene blue or Sudan red) was added to these compositions for visual assessment of the susceptibility to washing off the skin.

11 test subjects each received a 0.5 g sample of the composition containing the copolymer used according to the invention and a 0.5 g comparative sample but were unaware which was the sample according to the invention and which was the comparative sample. The samples were applied to the backs of both hands, which were freshly washed, and then a jet of water at 30° C. was directed onto the backs of the hands for 10 seconds, and subsequently the intensities of the colorations remaining on the backs of the hands were compared.

This was followed by all the test subjects washing the backs of their hands with water containing a detergent, namely a 10% by weight aqueous sodium lauryl ether sulfate solution, by continuous massage for 5 sec, and then briefly rinsing off the washing solution with water at 30° C. The intensities of the colorations on the backs of the hands were again compared.

The samples had the following compositions:
Sample 1 (according to the invention):

Water-in-oil cream containing methylene blue (viscosity: 10,000 mPa·s)

| Phase I: | 4.0% by weight | hydrogenated castor oil reacted with 7 mol of ethylene oxide |
| --- | --- | --- |
| | 3.0% by weight | mixture of polyglyceryl 2-sesquiisostearate, beeswax, mineral oil, magnesium stearate and aluminum stearate |
| | 2.0% by weight | microcrystalline wax |
| | 0.5% by weight | mixture of mineral oil and lanolin alcohol |
| | 8.0% by weight | isopropyl myristate |
| | 8.0% by weight | polypropylene glycol 3-myristyl ether |
| | 4.0% by weight | cetylstearyl 2-ethylhexanoate |
| | 4.0% by weight | liquid paraffin |
| | 3.0% by weight | polyethylene glycol/dodecyl glycol copolymer |
| | 3.0% by weight | hydroxyoctacosanyl hydroxystearate |
| | 3.0% by weight | 2-hydroxy-4-methoxybenzophenone |
| | 1.0% by weight | aluminum stearate |
| | 4.0% by weight | styrene/butadiene copolymer |
| Phase II: | 5.0% by weight | 1,2-propylene glycol |
| | 3.0% by weight | ethyl p-aminobenzoate reacted with 25 mol of ethylene oxide |
| | 0.2% by weight | methyl- and propylparabens |
| | 0.3% by weight | imidazolidinylurea |
| | 43.5% by weight | water |
| | 0.5% by weight | methylene blue |

Sample A (comparative):

Water-in-oil cream containing methylene blue (viscosity: 600 mPa·s) as sample 1 but without styrene/butadiene copolymer and with 8.0% by weight in place of 4.0% by weight cetylstearyl 2-ethylehxanoate.

Sample 2 (according to the invention):

Water-in-oil cream containing Sudan red (viscosity: 18,000 mPa·s) as sample 1 but with 0.5% by weight Sudan red in phase I in place of 0.5% by weight methylene blue in phase II.

Sample B (comparative):

Water-in-oil cream containing Sudan red (viscosity: 700 mPa·s) as sample 2 but without styrene/butadiene copolymer and with 8.0% by weight in place of 4.0% by weight cetylstearyl 2-ethylhexanoate.

Sample 3 (according to the invention):

Oil-in-water cream containing Sudan red (viscosity: 3,000 mPa·s)

| Phase I: | 1.0% by weight | a mixture of stearyl alcohol and cetylstearyl alcohol reacted with 6 mol of ethylene oxide |
| --- | --- | --- |
| | 1.0% by weight | cetylstearyl alcohol reacted with 25 mol of ethylene oxide |
| | 3.0% by weight | glyceryl stearate |
| | 0.2% by weight | (−)-2-bisabolol |

-continued

| | 5.0% by weight | liquid paraffin |
| --- | --- | --- |
| | 10.0% by weight | $C_{12}$-$C_{15}$-alkyl benzoate |
| | 5.0% by weight | jojoba oil |
| | 0.2% by weight | α-tocopherol |
| | 2.0% by weight | cetylstearyl alcohol |
| | 3.0% by weight | 2-hydroxy-4-methoxybenzophenone |
| | 5.0% by weight | cetylstearyl 2-ethylhexanoate |
| | 4.0% by weight | styrene/butadiene copolymer |
| | 0.5% by weight | Sudan red |
| Phase II: | 3.0% by weight | 1,2-propylene glycol |
| | 2.0% by weight | 2-hydroxy-4-methoxybenzophenone-5-sulfonic acid |
| | 1.0% by weight | triethanolamine |
| | 0.3% by weight | imidazolidinylurea |
| | 0.2% by weight | methyl- and propylparabens |
| | 53.6% by weight | water |

Sample C (comparative):

Oil-in-water cream containing Sudan red (viscosity: 4,500 mPa·s) as sample 3 but without styrene/butadiene copolymer and with 9.0% by weight in place of 5.0% by weight cetylstearyl 2-ethylhexanoate.

Table 1 shows the results of the tests. Indicated in each case are the number of times the coloration with the sample according to the invention was assessed as distinctly more intense than the coloration with the comparative sample after washing with pure water and with water containing detergent without knowing which was the sample according to the invention and which was the comparative sample.

TABLE 1

| | | Number assessed as more intense for |  |
| --- | --- | --- | --- |
| | | | washing with |
| sample | than | comparative sample | pure water | water with detergent |
| 1 | | A | 10 of 11 | 9 of 11 |
| 2 | | B | 10 of 11 | 10 of 11 |
| 3 | | C | 5 of 11 | 4 of 11 |

EXAMPLE 2

BARRIER EFFECT OF LIQUID PARAFFIN COMPOSITIONS

To assess the barrier effect, a composition containing 8% by weight styrene/butadiene copolymer from Example 1 in liquid paraffin was prepared (sample 4). This was compared with liquid paraffin thickened with an by weight highly disperse silica to produce a comparable viscosity (sample D).

Both forearms of 5 test subjects were painted with 1% by weight aqueous bromothymol blue solution and then covered with the sample on one arm and with the comparative sample on the other arm. 0.1 normal aqueous sodium hydroxide solution was applied to the treated areas of skin. It was possible to follow the penetration through the liquid paraffin composition by the blue coloration of the indicator dye.

Table 2 shows the times until the blue coloration first appeared and until coloration was complete when sample 4 according to the invention and comparative sample D were used.

TABLE 2

| Test subject | Times for blue coloration to appear | |
|---|---|---|
| | Time [sec] until blue coloration first appeared | coloration complete |
| Sample 4: | | |
| 1 | 35 | >120 |
| 2 | 35 | >120 |
| 3 | 50 | >120 |
| 4 | 65 | >120 |
| 5 | 40 | >120 |
| Comparative sample D: | | |
| 1 | 10 | 50 |
| 2 | 15 | 60 |
| 3 | 12 | 60 |
| 4 | 35 | 120 |
| 5 | 15 | 60 |

We claim:

1. A cosmetic composition which forms a layer that is not easily washed off skin with water, consisting essentially of 1-20 wt. % of a random copolymer having a molecular weight of 75,000-130,000 composed of 50-65 wt. % of styrene, 30-50 wt. % butadiene and 0-5 wt. % of other copolymerizable monomers, wherein at least 97% of the olefinic double bonds in said copolymer have been hydrogenated and not more than 5% of the aromatic unsaturations are hydrogenated; mixed in an oil-in-water or a water-in-oil emulsion containing an effective amount of a cosmetically active component.

2. The composition of claim 1 wherein said copolymer is composed of 52-57 wt. % styrene, 43-48 wt. % butadiene and 0-5 wt. % of other copolymerizable monomers.

3. A process for the topical application of a cosmetic comprising: forming a layer which is not easily washed off skin with water by applying an effective amount of the composition of claim 1 to a subject in need thereof in need thereof.

4. A process for the manufacture of a cosmetic composition that forms a layer which is not easily washed off skin with water consisting essentially of: adding 1-20 wt. % of a random copolymer having a molecular weight of 75,000-130,000 composed of 50-65 wt. % of styrene, 30-50 wt. % of butadiene and 0.14 5 wt. % of other copolymerizable monomers, wherein at least 97% of the olefinic double bonds in said copolymer have been hydrogenated, and not more than 5% of the aromatic unsaturations are hydrogenated to an oil-in-water or a water in oil emulsion containing an effective amount of cosmetically active component.

5. The process of claim 4 wherein said copolymer is composed of 52-57 wt. % of styrene, 43-48 wt. % of butadiene, and 0-5 wt. % of other copolymerizable monomers.

* * * * *